United States Patent
West et al.

(10) Patent No.: US 7,276,142 B2
(45) Date of Patent: Oct. 2, 2007

(54) COMBINATION PH ELECTRODE WITH STABLE STANDARD POTENTIAL

(75) Inventors: Steven J. West, Hull, MA (US); Moshe Hirshberg, Brookline, MA (US)

(73) Assignee: Thermo Orion Inc., Beverly, MA (US)

( * ) Notice: Subject to any disclaimer, the term of this patent is extended or adjusted under 35 U.S.C. 154(b) by 412 days.

(21) Appl. No.: 10/074,219

(22) Filed: Feb. 12, 2002

(65) Prior Publication Data

US 2003/0150726 A1    Aug. 14, 2003

(51) Int. Cl.
G01N 27/36    (2006.01)
G01N 27/403    (2006.01)

(52) U.S. Cl. .................................... 204/433; 204/435

(58) Field of Classification Search .............. 204/280, 204/408, 420, 433, 435; 324/438
See application file for complete search history.

(56) References Cited

U.S. PATENT DOCUMENTS

| | | | | |
|---|---|---|---|---|
| 4,495,050 A | | 1/1985 | Ross, Jr. .................... 204/408 |
| 4,543,175 A | * | 9/1985 | Subsara et al. ............. 204/400 |
| 4,608,148 A | * | 8/1986 | Frollini et al. ............. 204/408 |
| 5,143,621 A | * | 9/1992 | Bartram et al. ............ 210/690 |
| 5,160,420 A | * | 11/1992 | Marsoner et al. ........... 204/433 |
| 5,362,577 A | * | 11/1994 | Pedicini ....................... 429/27 |
| 5,575,769 A | * | 11/1996 | Vaillancourt ................. 604/86 |
| 6,350,367 B1 | | 2/2002 | West ........................... 205/775 |

OTHER PUBLICATIONS

Aldrich Chemical Company, Inc. Catalog of Chemicals, 1992, p. 1990.*
West, S.J., et al., *Ultrapure Water*, vol. 15, No. 10, pp. 45-52 (1998).

* cited by examiner

Primary Examiner—Kaj K. Olsen (57) ABSTRACT

Disclosed are combination glass pH electrodes, the standard potential of which is stabilized by means one or more of the following structural modifications:
(a) incorporating a noble metal internal element in the pH half-cell;
(b) incorporating a noble metal internal element in the reference half-cell;
(c) incorporating an internal pH bulb electrolyte with stable pH and oxidation-reduction potential;
(d) incorporating an homogenous reference electrolyte with stable oxidation-reduction potential and equitransferent salt;
(e) incorporating a liquid junction composed of a porous, inert material;
(f) incorporating a reference electrolyte compartment vent;
(g) incorporating a storage sleeve, with or without an absorbent medium located therein.

4 Claims, 7 Drawing Sheets

Combination pH Electrode with Alternative Venting System (18) Reference Electrolyte Compartment Septum Closure (21) Slit in Reference Electrolyte Compartment Septum Closure (17) Opening in Reference Electrolyte Compartment (Outer Tube)

FIGURE 1 Basic Elements of Combination pH Electrode

FIGURE 2 Detail of pH Half-Cell Assembly

FIGURE 3 Combination pH Electrode with Alternative Venting System

FIGURE 4 Front View of Septum Closure with Alternative Venting system

FIGURE 5 Combination pH Electrode and Storage Sleeve

Figure 6 - GRAPH 1  Standard Potential Drift with Vent of Current Invention

FIGURE 7 - GRAPH 2 Standard Potential Drift without Vent of Current Invention

COMBINATION PH ELECTRODE WITH STABLE STANDARD POTENTIAL

FIELD OF THE INVENTION

It is well known that electrodes for the measurement of pH need to be calibrated regularly in pH buffers to compensate for drift in the standard potential. Calibration is inconvenient and time-consuming. In this invention we describe how a study of the contributions to drift of the standard potential led to innovations and improvements in the design of a combination pH electrode such that the stability over time of the standard potential is improved resulting in a reduction in the frequency of calibration required to maintain a desired accuracy.

BACKGROUND OF THE INVENTION

Combination pH Electrodes:

A combination pH electrode is one in which the sensing and reference half-cells are integrated into a single assembly, usually a cylindrical probe for dipping into a test solution. For the purposes of the following descriptions and explanations, the standard potential can be defined as the potential in any certified standard. Here, the potential in pH 7.00 buffer as test solution will be used. The potential, or strictly speaking "potential difference", of a combination pH electrode in a solution is actually an algebraic sum of at least five potential differences, henceforth referred to simply as potentials. These potentials are defined as follows:

| Potential | Description |
| --- | --- |
| E1 | Potential between inner metal element of pH half-cell and electrolyte in the glass pH bulb. Depends on identity of metal and composition of pH bulb electrolyte. |
| E2 | Potential between pH bulb electrolyte and glass of pH bulb. Depends on pH of pH bulb electrolyte. |
| E3 | Potential between glass of bulb and test solution. Depends on pH of test solution. |
| E4 | Potential at junction of test solution and inner reference half-cell electrolyte (commonly known as junction or liquid-junction potential) Depends on compositions of test solution and reference electrolyte. |
| E5 | Potential between reference half-cell electrolyte and inner metal element of reference half-cell. Depends on identity of metal and composition if reference half-cell electrolyte. |

Symmetrical Cells:

In order for the standard potential to be stable, all five of these potentials must be stable. Usually, electrode designers strive toward a system where the standard potential, i.e., the algebraic sum of these five potentials, equals zero in a test solution having a pH of 7.00. Since pH 7.00 is considered neutral, a standard potential of zero is convenient for the designers of meters that measure the potential, and there are advantages with regard to the effect of temperature on the potential that will become clear as this description advances.

Unless otherwise noted, all electrodes discussed herein will be so-called "symmetrical cells", those where a design goal is a potential close to zero millivolts at pH 7.00.

In a symmetrical cell, the metal elements in the pH and reference half-cells are the same and the potential-determining components of the pH bulb electrolyte and reference electrolyte are the same. Potentials E1 and E5 are thus equal in magnitude but opposite in sign and cancel. Similarly, by adjusting the pH of the pH bulb electrolyte to 7.00, potentials E2 and E3 become equal in magnitude and opposite in sign and also cancel, unless a small difference known as the asymmetry potential is present as discussed below. E4, the junction potential, cannot be entirely eliminated but can be minimized if a high concentration of equitransferent salt is included in the reference electrolyte. This is also discussed further below. Thus, in symmetrical cells, the problem of maintaining as stable a standard potential as possible over time, so as minimize the need to recalibrate frequently, is often equivalent to maintaining a standard potential of zero.

Asymmetry and Junction Potentials:

A brief discussion of asymmetry and junction potentials is in order. The asymmetry potential across the pH-sensitive glass is any non-zero potential difference that exists when the pH values of the solutions on both sides of the glass are equal. An experiment can be designed to measure asymmetry potentials. A solution can be split into two portions, isolated by pH sensitive glass, and the potential between two identical reference electrodes placed in the two portions of solution can be measured to yield the asymmetry potential. However, in practice, measurement of the asymmetry potential in a combination pH probe is not always possible. For example, if a symmetrical cell is devised, in which the pH bulb electrolyte is adjusted to 7.00 and the potential of the probe is measured in pH 7.00 buffer, a non-zero potential might be ascribed to asymmetry potential or to junction potential or both. The pH 7.00 buffer does not contain the components required to establish potentials E1 and E5, so the pH bulb electrolyte and the reference electrolyte must necessarily have a different composition than 7.00 buffer. This creates two inevitable uncertainties.

First, the junction potential between the reference electrolyte and the 7.00 buffer will be unknown. Junction potentials can be estimated theoretically, but cannot in most cases be measured because another uncertain potential is always introduced into any cell that is conceived to attempt a junction potential measurement. This is a fundamental dilemma of electrochemical cells (Bates, R. G., *Determination of pH: Theory and Practice*, $2^{nd}$ Ed., John Wiley & Sons, New York, p. 33 and elsewhere).

Second, an uncertainty in the pH value of the bulb electrolyte is always present. This is because its pH was adjusted through comparison to a 7.00 buffer with some other pH cell, the junction potential of which cannot be assumed to be the same in pH 7.00 buffer and in the pH bulb electrolyte. Some uncertainty may even exist in the perfect cancellation of potentials E1 and E5 because the presence of a buffer substance in the pH bulb electrolyte, that may not be present in the reference electrolyte, may alter the activity of the components that determine E1 and E5. Often, this problem is overcome by saturating each electrolyte with these potential-determining components such that their activity is fixed at the saturation level.

Temperature Effects:

It is not within the scope of this specification to go into great detail about temperature effects on pH cells, but brief mention is appropriate since temperature will play a role in parts of the discussion. It's clear why a symmetrical cell is desirable when considering the effect of temperature. To the extent that potentials E1 and E5, as well E2 and E3, have essentially the same half-cell composition, temperature changes will affect them equally and cancel. This leaves E4, the junction potential, as potentially contributing to a change in standard potential as temperature changes. Suffice to say at this stage that the best approach to resolving the issue of temperature effect on E4 is to design cells with smallest junction potential achievable.

SUMMARY OF THE INVENTION

The present invention is thus directed to a combination glass pH electrode, the standard potential of which is stabilized by means one or more of the following structural modifications:

(a) incorporating a noble metal internal element in the pH half-cell, said noble metal by reason of its inertness maintaining its purity of composition and not degrading the purity of composition of solutions in contact with it;

(b) incorporating the same noble metal internal element in the reference half-cell as in the pH half-cell, said noble metal by reason of its inertness maintaining its purity of composition and not degrading the purity of composition of solutions in contact with it;

(c) incorporating an internal pH bulb electrolyte with stable pH and oxidation-reduction potential, said electrolyte by reason of its stable pH maintaining a stable interfacial potential at a pH-sensitive glass surface and by reason of its stable oxidation-reduction potential maintaining a stable electrochemical potential in contact with a noble metal;

(d) incorporating an homogenous reference electrolyte with stable oxidation-reduction potential and equitransferent salt, said electrolyte by reason of its stable oxidation-reduction potential maintaining a stable electrochemical potential in contact with a noble metal and by means of its equitransference maintaining a low and stable junction potential in contact with an electrolyte of differing composition;

(e) incorporating a liquid junction composed of a porous, inert material;

(f) incorporating a reference electrolyte compartment vent that minimizes moisture loss or pick-up from the surroundings yet admits sufficient air to permit flow of reference electrolyte through the liquid junction under the influence of gravity;

(g) incorporating a storage sleeve into which the glass bulb, liquid junction, and vent portions of the electrode can be sealed such that moisture loss is eliminated during storage; and/or (h) incorporating an absorbent medium located in the storage sleeve and in contact with the glass pH bulb such that said absorbent medium, when intentionally moistened with water or when becoming moistened due to reference electrolyte leaking from the electrode's liquid junction, serves to maintain high humidity in the interior of the storage sleeve and further serves to maintain the pH bulb in a hydrated state.

In certain preferred embodiments, the noble metal in the pH half-cell comprises platinum. Likewise, the noble metal in the reference half-cell preferably comprises platinum.

In certain preferred embodiments, the electrolyte in the pH half-cell comprises phosphate or borate buffer to stabilize the pH and a mixture of iodide and triiodide to stabilize the oxidation-reduction potential.

In certain preferred embodiments, the electrolyte in the pH half-cell has a pH slightly different from 7.00 in order to generate a potential across the pH bulb that cancels the potential across the liquid junction when the electrode is in pH 7.00 buffer so that the overall potential of the electrode is nearly zero.

In certain preferred embodiments, the electrolyte composition in the pH half-cell comprises 4 M KI, 0.0069 M $KI_3$, 0.2 M $H_3BO_3$, adjusted to pH 7.05 with KOH.

In certain preferred embodiments, the electrolyte in the reference half-cell comprises phosphate or borate buffer and a mixture of iodide and triiodide to stabilize the oxidation-reduction potential.

In certain preferred embodiments, the electrolyte composition in the reference half-cell comprises 4 M KI, 0.0069 M $KI_3$, 0.2 M $H_3BO_3$, adjusted to pH 7.05 with KOH.

In certain preferred embodiments, the porous, inert material comprises porous ceramic.

In certain preferred embodiments, the opening to the reference electrolyte compartment is covered with an elastomeric septum closure that is perforated to permit insertion of a tube which by reason of its small inside diameter compared to its length serves to reduce the rate at which moisture can diffuse into or out of the electrolyte compartment yet serves to permit sufficient ingress of air to allow electrolyte flow from the compartment through the liquid junction under the influence of gravity. Advantageously the tube in the septum has an inner diameter of about 0.5 mm and a length of about 10 mm.

In certain preferred embodiments, the opening to the reference electrolyte compartment is covered with an elastomeric septum closure with a slit, said slit by reason of the substantial but not absolute barrier it provides between the compartment and outside environment serving to retard diffusion of moisture into or out of the electrolyte compartment yet serving to permit sufficient ingress of air to allow electrolyte flow from the compartment through the liquid junction under the influence of gravity and at the same time serving to allow convenient replenishment of electrolyte by any liquid delivery means with delivery tip shaped so as to be able to pry open the slit, said slit then closing upon removal of delivery tip by reason of the restorative tendency of the elastomeric closure material. Advantageously the material of the septum closure may be, but is not limited to, silicone elastomer with a durometer of from about 30 to about 45.

In certain preferred embodiments the storage sleeve seal between the sleeve and electrode may be effected in a manner not limited to the following: the sleeve is composed of an elastomeric material having a durometer between 75 and 80, and forms a seal with the electrode cap upon insertion of the electrode into the sleeve.

In certain preferred embodiments, the absorbent material in the storage sleeve comprises glass wool.

Stability of Standard Potential:

The standard potential, which we will simply refer to as E, is the algebraic sum of 5 potentials:

$$E=E1+E2+(-E3)+E4+(-E5) \quad \text{EQUATION 1}$$

E3 and E5 are given minus signs in order to reflect the fact that they are measured in the opposite sense from their counterparts E2 and E1. For example, E2 can be thought of as the potential from the solution (pH bulb electrolyte) to the glass, and E3 from the glass to the solution (pH 7.00 buffer). E1 can be thought of as the potential from the metal to the solution (pH bulb electrolyte) and E5 from the solution (reference electrolyte) to the metal.

The stability of E is the sum of the stabilities of these 5 potentials. Therefore, the ensuing discussion will focus on the factors that contribute to instability of each of these potentials. Innovations will be presented for stabilization of these potentials. These innovations form the basis of the claims in this application.

DETAILED DESCRIPTION OF THE PREFERRED EMBODIMENTS

Figure 1:
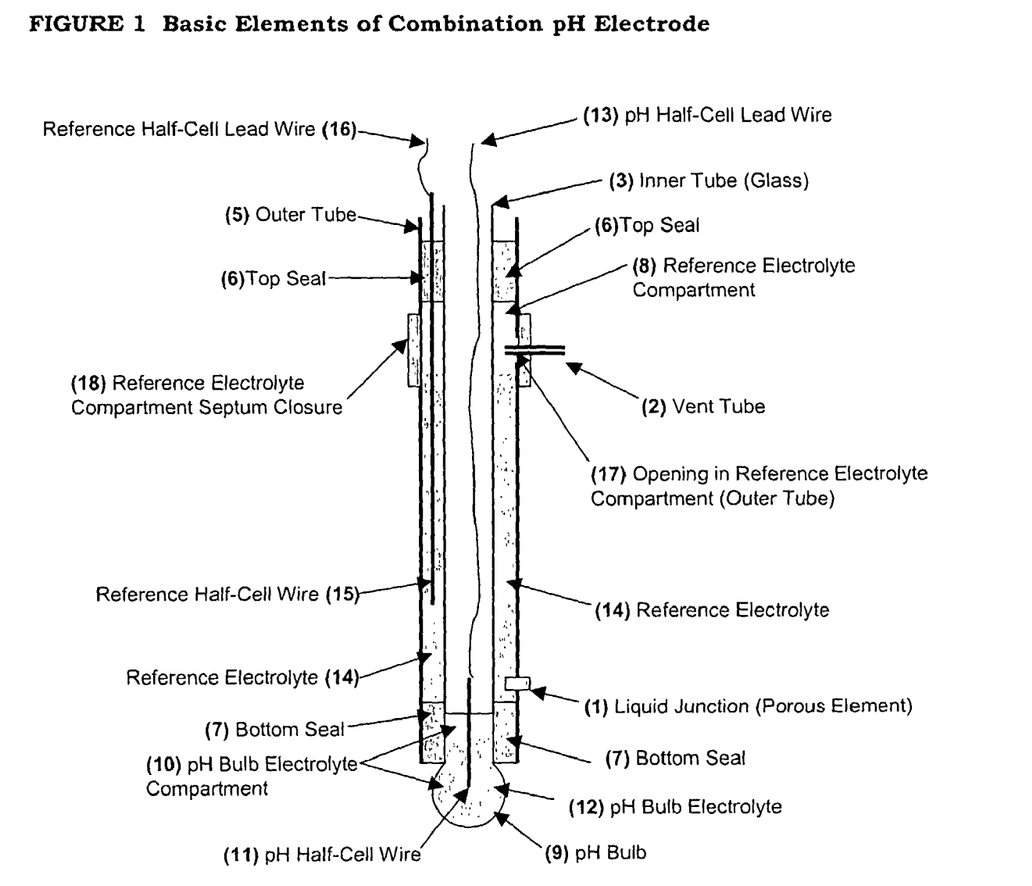
FIG. 1 depicts the essential elements of the combination pH electrode of the present invention.

As set forth above, FIG. 1 depicts the essential elements of the combination pH electrode of the present invention. As shown therein, the device has cylindrical symmetry with the exception of the porous liquid junction (1) and the vent tube (2) in the septum closure so it is presented as a cross section through the cylinder axis, intersecting elements (1) and (2), and therefore showing all relevant features of the cell.

The basic construction is that of two concentric tubes: an inner tube (3) of inert material, usually glass, onto the end of which is attached the glass pH bulb (9); and an outer tube (5) of inert material such as glass or plastic that houses the inner tube with a top seal (6) and bottom seal (7) that serve to maintain a concentric orientation of the inner and outer tubes (3) and (5) and create an reference electrolyte compartment (8) in the annulus.

It should be noted that seals (6) and (7) could be elastomeric components and might therefore appear as in the drawing, or, if both the inner and outer tubes (3) and (5) were of a material such as glass, seals could be affected by heat bonding such that no discrete seal components would be necessary. Other means of sealing or creating the basic construction could of course be conceived by others versed in the art.

The pH bulb (9) forms part of the pH bulb electrolyte compartment (10) into which are sealed the pH half-cell wire (11) and pH bulb electrolyte (12). An ordinary lead wire (13) is attached to the pH half-cell wire and runs up through the inner tube (3). The basics of this type of pH half-cell construction are well known to those versed in the art.

Reference electrolyte (14) and a reference half-cell wire (15) with lead wire (16) attached are shown in the reference electrolyte compartment (8). An opening (17) for replenishing the electrolyte is shown, covered by the septum closure (18) with vent tube (2), as referred to above. Also shown, as mentioned above, is a liquid junction (1) in the form of a porous plug.

Figure 2:
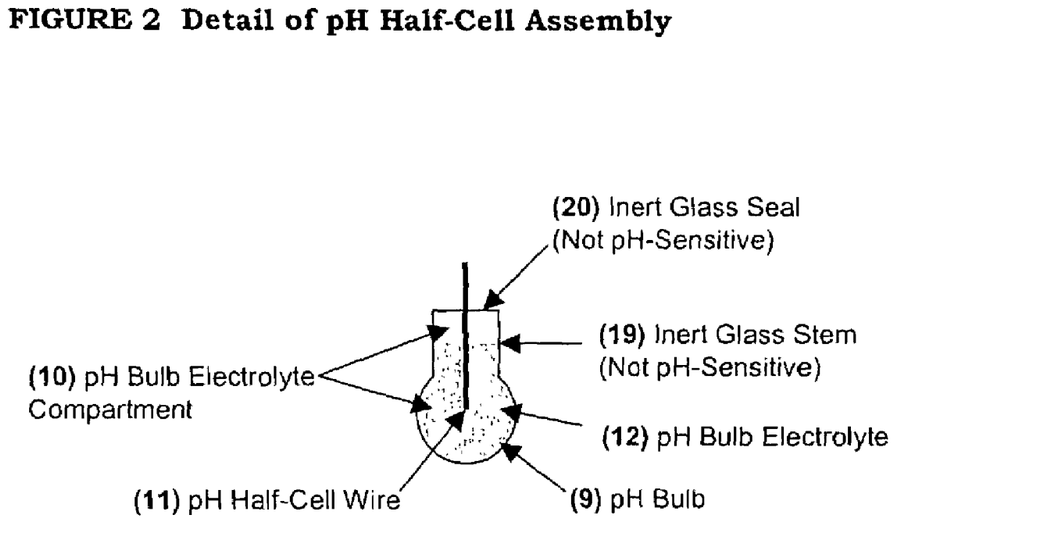
FIG. 2 is a detail of the pH half-cell assembly as shown in FIG. 1.

FIG. 2 is a detail of the pH half-cell assembly as shown in FIG. 1. Here the use of an inert (non-pH-sensitive) glass as stem (19) for forming the bulb and as seal (20) for enclosing the cell and wire is shown. Again, the construction of pH half-cells similar to the one shown is well known to those versed in the art.

Figure 3:
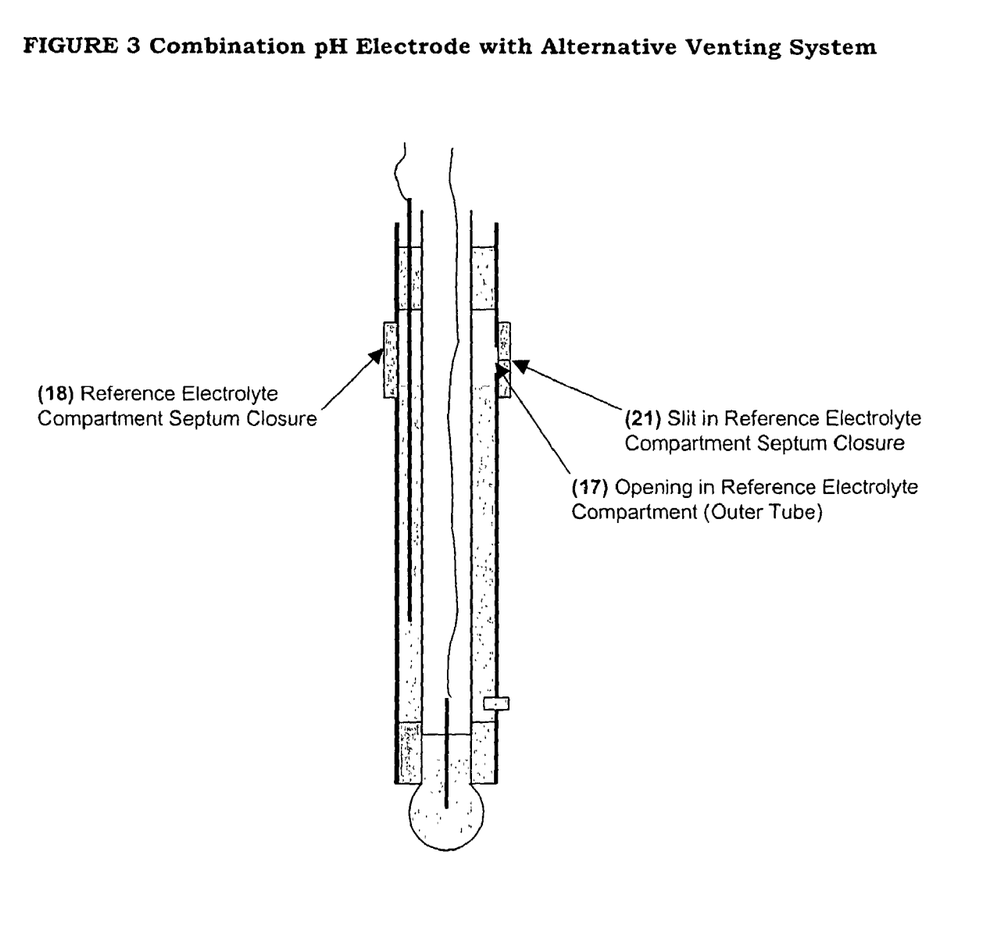
FIG. 3 is a variation on FIG. 1 where an alternative electrolyte compartment venting means is depicted.

FIG. 3 is a variation on FIG. 1 where an alternative electrolyte compartment venting means is depicted. Instead of the vent tube (2) of FIG. 1, a slit (21) in the septum closure is shown.

Figure 4:
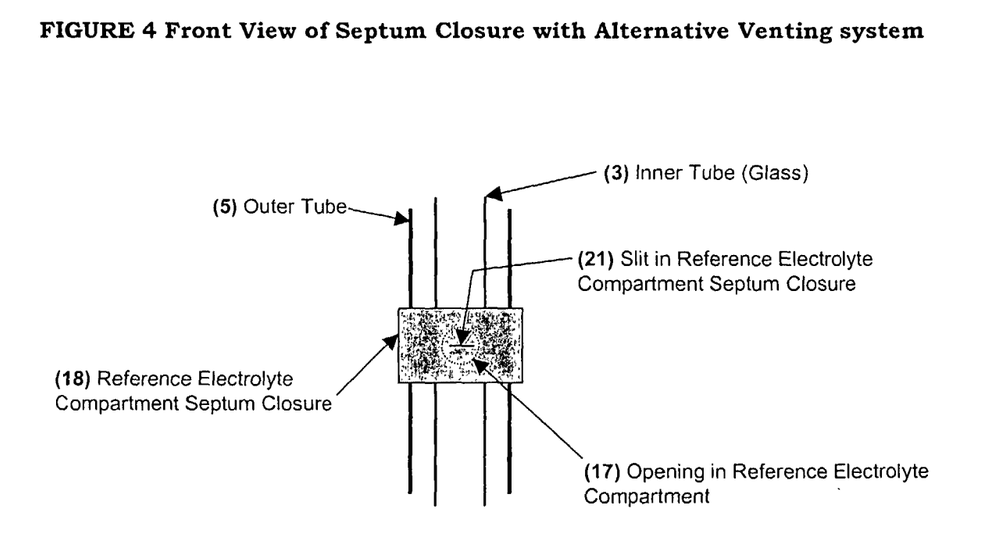
FIG. 4 is a front view of part of the combination electrode assembly of FIG. 3 showing the septum closure.

FIG. 4 is a front view of part of the combination electrode assembly of FIG. 3 showing the septum closure. The opening (17) in the outer tube (5) and slit (21) in the septum closure (18) are seen to better advantage in this view.

Figure 5:
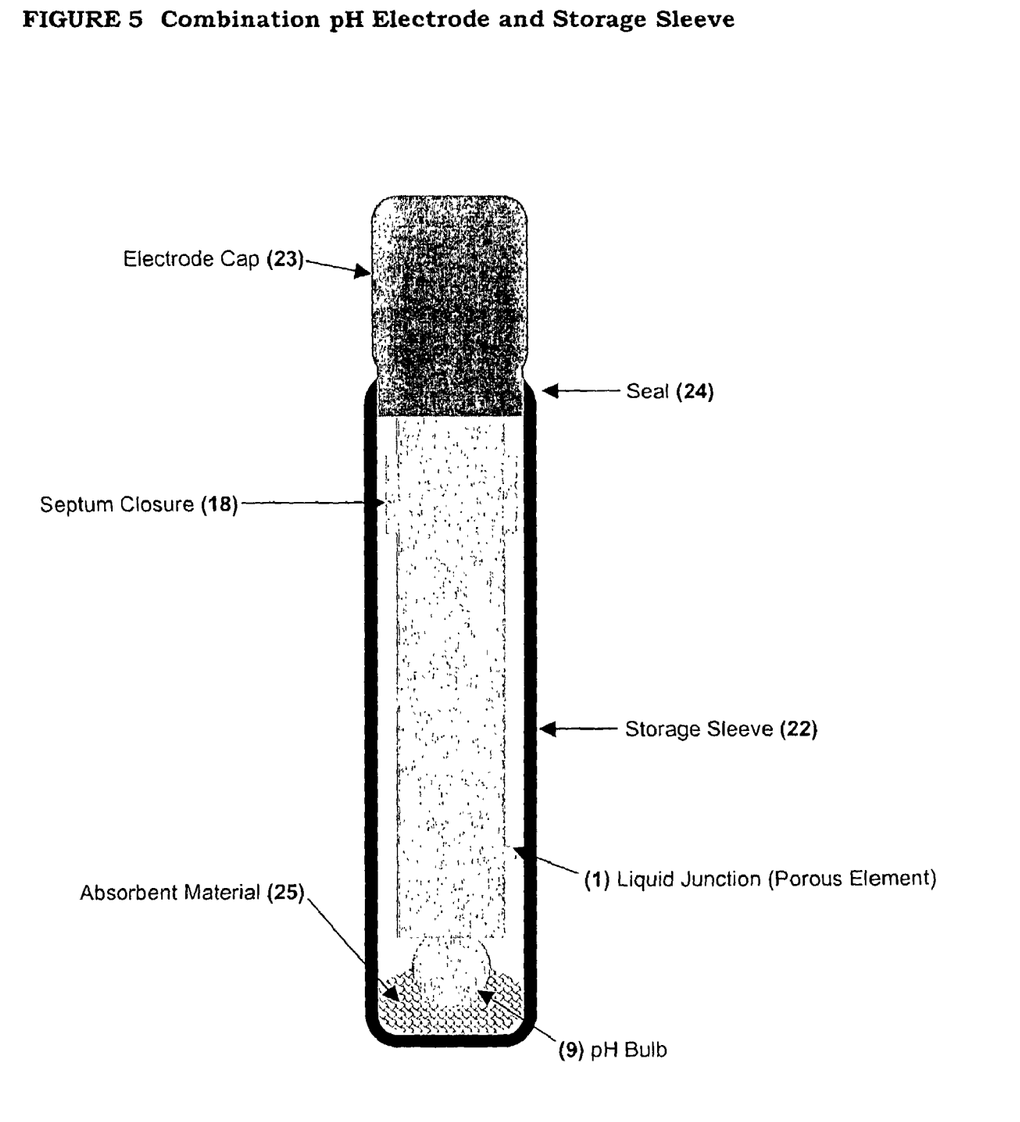
FIG. 5 shows the complete probe when inserted into a storage sleeve.

FIG. 5 shows the complete probe when inserted into the storage sleeve (22). The probe's cap (23) forms a seal (24) when the top of the elastomeric sleeve (22) is pushed over it. All of the elements of the pH and reference half-cells that would be affected by evaporation or pick-up of moisture, leakage, or dehydration—the septum closure (18), the liquid junction (1), and the pH bulb (9)—are enclosed in the sealed sleeve. In addition, an absorbent material (25) serves as a repository for moisture and keeps the pH bulb (9) moist when in contact with it.

Stability of E1:

E1 is an electrochemical half-cell potential developed between a metal and an electrolyte. Typically, the electrolyte is also saturated with a salt and in order to ensure saturation that salt is also present in its solid form. The most common half-cells are the silver-silver chloride and calomel half-cells.

Typical Internal Reference Half-Cells

| Metal | Sparingly soluble, saturated salt | Potential-determining ion(s) |
| --- | --- | --- |
| Silver | Silver chloride | Chloride (usually KCl, often saturated) |
| Mercury | Calomel (mercurous chloride) | Chloride (usually KCl, often saturated) |

In these half-cells, chloride ion activity in the presence of the saturated chloride salt of the metal (silver or mercury) determines the potential at the metal. In order for these half-cells to be stable over long time periods it is necessary for the chloride ion activity to remain constant. Factors that might change the chloride activity include loss or pick-up of water by evaporation, absorption of atmospheric moisture, or dilution with water or other solutions. In order to prevent these phenomena from changing the chloride activity, the soluble chloride salt in the electrolyte, usually KCl, is often present at saturation. In principle, this is a sound practice but in practice there are some disadvantages. Combination pH cells are used under widely variable conditions where temperature cannot be expected to be constant. The activity of chloride in these cells is determined by heterogeneous equilibrium or equlilibria—the solubility equilibrium between the solid sparingly soluble salt (and sometimes the soluble salt as well) and the solution. Heterogeneous equilibrium is achieved slowly after a perturbation such as a temperature change because transport by diffusion of ions between the solid salt and regions of solution that are not in direct contact is a slow process. Therefore, when temperature is changing even slightly, heterogeneous systems are often not in equilibrium. Even identical half-cells, if they are not in equilibrium, cannot be expected to have the same potential. The cancellation of potentials E1 and E5 cannot be relied upon to occur if the cells are not in equilibrium.

In U.S. Pat. No. 4,495,050, Ross described a half-cell with homogeneous electrolyte using triiodide/iodide as a redox potential buffer and borate as a pH buffer. This is a solution with a pH value that is stabilized by the buffering action or boric acid ($H_3BO_3$) and an oxidation-reduction potential that is stabilized by the buffering action of the triiodide/iodide redox couple. In a recent publication (West, S. J., et al., *Ultrapure Water*, Vol. 15, No. 10, pp. 45-52, 1998), it was demonstrated that half-cells of this type, in addition to being almost temperature invariant, achieve a stable, equilibrium potential much more rapidly than silver-silver chloride half-cells after a temperature perturbation. It has been also been demonstrated that homogeneous solutions of the type described by Ross, are stable for lengthy periods of time when maintained in a sealed glass or plastic vessel. See, commonly owned, application Ser. No. 09/178,011, now U.S. Pat. No. 6,350,367.

Stability of E5:

A disadvantage to the homogeneous half-cell composition is that there is no way to prevent the loss or pick-up of water from affecting the activity of the dissolved components that determine the potential. This is not problem in the stability of E1, but is a problem for E5 as described below. It is this disadvantage that led to one of the key features of the described invention.

The electrolyte that determines the potential E1 is sealed in a glass bulb. Therefore, loss or pick-up of water or contamination with other solutions cannot occur. E5 is more complicated. The reference half-cell electrolyte must be able to flow through the liquid junction in order to prevent back-diffusion of test solution into the junction. In cases considered here, flow through the liquid junction is driven by gravity. In order for flow to occur from the reference electrolyte compartment, the compartment must be vented to atmosphere. This vent provides a path through which water loss or pick-up might occur, altering the composition of the electrolyte over time.

In one embodiment of the present invention (see, FIG. 1), a narrow vent tube is inserted in the septum that covers the electrolyte compartment fill hole, which is typically about 3 mm in diameter. The vent tube, having an inner diameter of 0.5 mm or less and a length of approximately 10 mm, allows air into the chamber in order to permit flow of electrolyte, but presents a long narrow path for diffusion of water vapor into or out of the electrolyte compartment. In this manner the composition of the electrolyte is conserved. An inconvenient aspect of this venting system is that it is difficult to replenish the electrolyte. The vent tube must be removed for refilling and then put back in place.

In another embodiment (FIGS. 3 and 4), a slit of 2-mm length in the elastomeric septum serves to allow air ingress while preventing significant evaporative loss from or moisture pick-up by the electrolyte. This is because the slit in the septum is an effective barrier against diffusion, the mechanism through which evaporative loss and moisture pick-up occur, but the slit cannot prevent the ingress of air that is induced by means of the partial vacuum created in the electrolyte chamber as a result of the flow of electrolyte out of the chamber through the liquid junction under the force of gravity. In other words, the slit septum is effective against the passive transport of vapor by diffusion, but cannot prevent the active transport of fluid (air) forced by the gravitational head of the electrolyte. As electrolyte flows under gravity through the liquid junction, the vacuum that builds in the chamber opens the septum.

An advantage of the slit septum venting system is that it provides easy access for electrolyte replenishment. Any fluid delivery system with a small enough tip—a needle, a pipet tip, a bottle with a conically shaped tip—can be used to part the slit for replenishment and the slit will re-close after removal of the delivery tip. Furthermore, a common problem with fill holes for reference chambers is that they become encrusted with dried electrolyte. Insertion of the delivery tip serves to clean away such encrustation.

Thus, stabilization of E5 is accomplished by two means: first, a homogeneous electrolyte serves to maintain the system in equilibrium in spite of variations in temperature; second, a specially designed vent in the septum closure serves to allow air ingress to permit electrolyte flow but reduces loss or pick-up of moisture from the electrolyte by passive processes to a negligible amount.

Stabilization of E2 and E3:

Potentials E2 and E3 are the potentials between the pH-sensitive glass and the solutions on either side—the pH bulb electrolyte and the test solution, in this case a pH 7.00 buffer. pH-sensitive glass has been developed over the decades to a high degree of stability and selectivity, such that the stability of the potential between a modern, hydrated pH-sensitive glass and a standard buffer solution is for practical purposes dependent solely on the stability of the buffer solution. If the pH of the solution in question remains constant (at constant temperature of course), the potential will remain constant.

It has been discussed earlier that when the pH on both side of a pH-sensitive glass is the same, a potential difference called the asymmetry potential may persist, but in practical electrode designs this is not always possible to ascertain. As discussed below, if a non-zero junction potential is present (E4), it may be desirable to manipulate the pH of the pH-bulb electrolyte to a pH other than 7.00 in order that the overall combination electrode potential be zero millivolts when the test solution is pH 7.00.

In order to function properly, pH-sensitive glass must be conditioned or hydrated. pH glass membranes are usually fabricated by dipping an inert glass tube into molten pH glass and then blowing the pH glass into a bulb as it cools. After completion of the other steps in the fabrication of an entire electrode assembly, the glass needs to be exposed to aqueous solution for some time, typically 24 to 48 hours, in order to become hydrated. It is only in the hydrated state that stable, reproducible behavior can be expected. If left in dry air, the glass can become dehydrated and require rehydration in order to function properly again. A convenient accessory to the present invention is a storage sleeve that maintains the glass in a hydrated state when not in use (FIG. 5). A moist wad of fiber in the sleeve has been demonstrated to maintain hydration without the inconvenience of free-flowing liquid water that could spill or leak out. In order to maintain the moistness of the wad of fiber, the sleeve forms a seal with the electrode cap, thus maintaining a humid environment all around the probe. Santoprene 101-80 elastomer with a durometer between 75 and 85, available from Advanced Elastomer Systems, Akron, Ohio, is an appropriate material for the sleeve to form a good seal when pushed over the cap as shown in FIG. 5.

The sleeve serves a secondary purpose of providing an additional barrier to evaporation of reference half-cell electrolyte that could occur in spite of the specially vented septum closure described above if the electrode is stored for lengthy periods of time. The ability to maintain a stable potential during lengthy periods of storage is desirable since electrodes may languish on warehouse shelves and then be expected to give accurate readings immediately "out of the box" at the point of use.

Stability of E4:

The stability of E4, the liquid junction potential, has been found most effectively by electrochemists to be enhanced by using a reference half-cell electrolyte that has as high a concentration of equitransferent salt as possible. Equitransferent salts are those where the anion and cation ion have equal mobilities. The most commonly used equitransferent salt is potassium chloride, but other equitransferent salts such as potassium nitrate, potassium iodide, and ammonium sulfate are also useful for this purpose. As with the asymmetry potential, it is not always possible to ascertain the value of the junction potential in practical, combination pH cells. As seen in the example below, the idea of allowing the asymmetry and junction potentials to compensate so that the overall cell potential is zero with a test solution at pH 7.00 has been exploited in this invention.

EXAMPLES

Electrodes conforming to the descriptions and drawings in this application were built and tested for stability of their standard potential. Referring once again to the drawings, the following specific materials and compositions were used for the critical design elements, though it will be recognized by those versed in the art that other choices of materials and compositions might also serve.

The outer tube was glass with an outside diameter of 12 mm and a wall thickness of 1 mm. The opening or fill hole was 3 mm in diameter. The inner tube was glass with an outside diameter of 3.6 mm and a wall thickness of 0.8 mm. The pH half-cell wire and reference half-cell wire were platinum, a noble metal which by reason of its inertness maintains its purity of composition and does not degrade the purity of composition of solutions in contact with it.

The pH bulb and reference electrolyte had the following composition: 4 M KI, 0.0069 M KI$_3$, 0.2 M H$_3$BO$_3$, adjusted to pH 7.05 with KOH. The liquid junction material was porous ceramic, supplied by Analytical Measurements LTD in Peltham, Middlesex, England, heat bonded into the outer glass tube. The septum closure was made of silicone elastomer with a durometer of 30 to 45. The septum was perforated over the opening in the outer tube so that a PTFE tube, 0.5 mm inner diameter and 10 mm in length could be inserted in the manner depicted in FIG. 1. Both the inner and outer tubes were made of glass. The upper seal was a silicone elastomer with durometer of 30 to 45 and the bottom seal was affected by heat bonding of the glass tubes.

Figure 6:
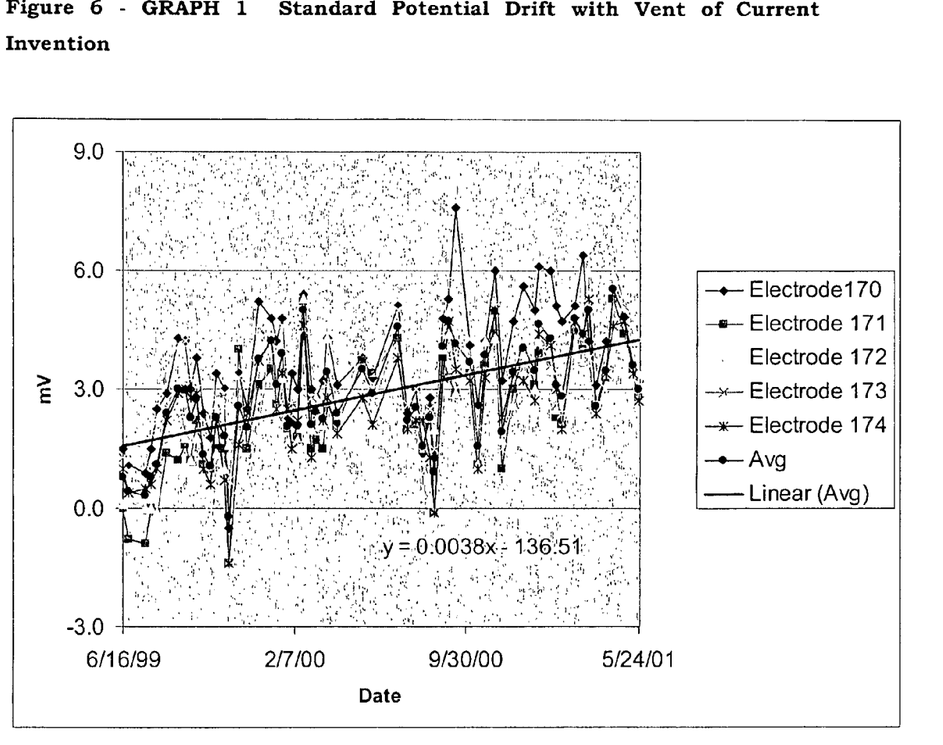
FIG. 6 is GRAPH 1, which shows variations in Standard Potential Drift with Vent of Current Invention.

The standard potentials as a function of time of five electrodes are displayed in FIG. 6, GRAPH 1. Measurements were made by placing the electrodes in a pH 7.00 buffer and recording the potential after 5 minutes with a pH meter. Between measurements the electrodes were stored in de-ionized water. Reference electrolyte was maintained at a level higher than the test solutions by adding more as needed. A linear regression of the average of the five potentials yielded the equation on the graph. The equation indicates that the average drift rate was +0.0038 mV/day over the approximately two-year period the electrodes were tested. This is equivalent to about 1.4 mV/year or a pH change of about 0.02 pH units per year. The required accuracy for many, if not most, pH measurements is about 0.1 pH units. This means that such an electrode could go for a year without calibration and still meet stringent accuracy requirements. Furthermore, the absolute average potential after nearly two years was about +4 mV. This corresponds to a pH value of about 7.07 when read on a meter that has never been calibrated, such that a potential of 0.0 mV will give a reading of pH 7.00. Thus, good accuracy can be obtained with these electrodes without any calibration, provided they are stored in water and the reference electrolyte is replenished at appropriate intervals.

Figure 7:
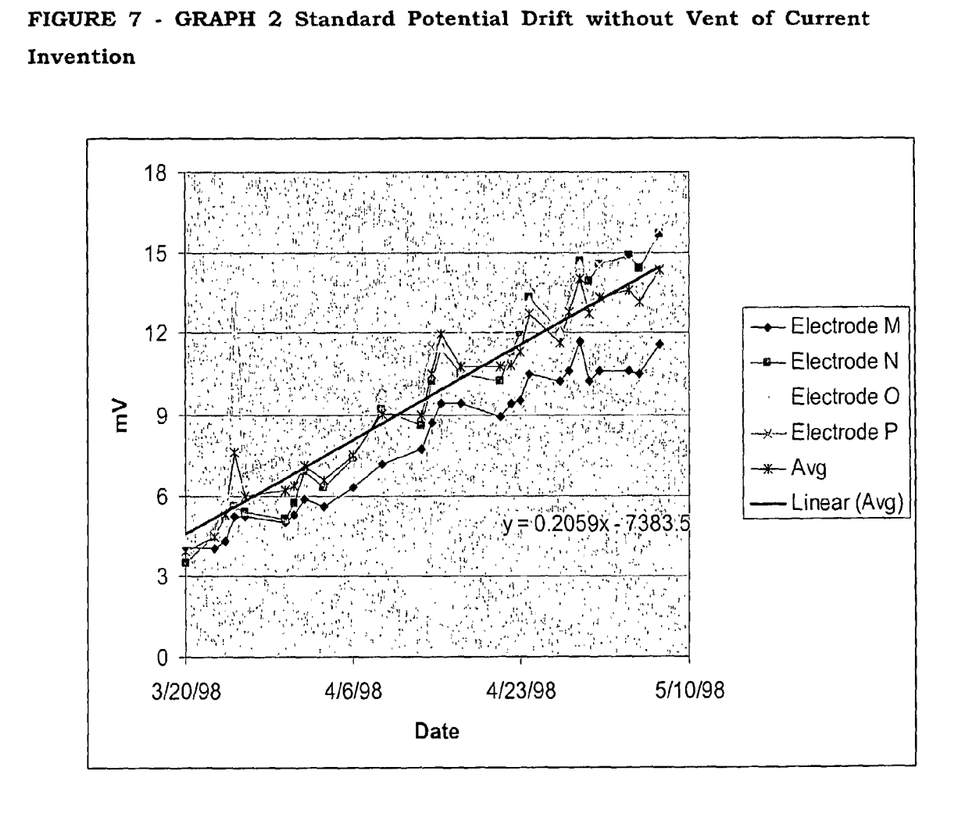
FIG. 7 is GRAPH 2, which shows variations in Standard Potential Drift without Vent of Current Invention.

Compare these results to those in FIG. 7, GRAPH 2. The electrodes in GRAPH 2 were treated identically, but the electrolyte compartment fill holes were left open to the atmosphere. Here, the average drift rate was about +0.2 mV/day. This is equivalent to about 70 mV/year, or about 1.2 pH units.

The Nernst Equation for the reference half-cell potential of these electrodes is the following:

$$E5 = E0 + 29 \cdot \log\left[\frac{(I_3^{-1})}{(I^{-1})^3}\right] \qquad \text{EQUATION 2}$$

where E5 is the reference half-cell potential, E0 is a constant, $(I_3^{-1})$ is the concentration of triiodide ion in the reference electrolyte in moles per liter and ($I^{-1}$) is the concentration of iodide ion in the reference electrolyte in moles per liter. Evaporation of water from the electrolyte used in these tests would increase the concentrations of triiodide and iodide equally, but since the concentration of iodide is cubed in the denominator of the log term, the reference half-cell potential will be decreased. From EQUATION 1 it is evident that a decrease in reference half-cell potential, E5, will result in an increase in the overall cell potential, E.

Thus it can be seen how devising a fill hole closure that reduces evaporation can improve the stability of the standard potential over time.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A combination glass pH electrode including a sensing electrode, a reference electrode possessing a standard potential, an outer tube having a liquid junction, an inner tube centrally located within the outer tube and connected to the outer tube by a top seal and a bottom seal, a reference electrolyte compartment located between the inner and outer tubes and the top and bottom seals having an opening in the outer tube, and reference electrolyte within the reference electrolyte compartment, wherein the improvement comprises:

incorporation of a reference electrolyte compartment vent wherein the opening to the reference electrolyte compartment is covered with an elastomeric septum closure that is perforated to permit insertion of a tube which by reason of its small inside diameter compared to its length serves to minimize diffusion of moisture into or out of the reference electrolyte compartment yet serves to admit sufficient air to allow electrolyte flow from the reference electrolyte compartment through the liquid junction under the influence of gravity;

whereby the reference electrolyte is kept constant and the standard potential of the reference electrode is thereby stabilized;

whereby the combination glass pH electrode needs no calibration for up to two years.

2. An electrode as in claim 1, further comprising a removable tube inserted into the perforation of the elastomeric septum closure, said tube having an inner diameter of about 0.5 mm and a length of about 10 mm, said tube being temporarily removed in order to replenish the reference electrolyte.

3. A combination glass pH electrode including a sensing electrode, a reference electrode possessing a standard potential, an outer tube having a liquid junction, an inner tube centrally located within the outer tube and connected to the outer tube by a top seal and a bottom seal, a reference electrolyte compartment located between the inner and outer tubes and the top and bottom seals having an opening in the outer tube, and reference electrolyte within the reference electrolyte compartment, wherein the improvement comprises:

incorporation of a reference electrolyte compartment vent wherein the opening to the reference electrolyte compartment is covered with an elastomeric septum closure with a slit, said slit by reason of the substantial but not absolute barrier it provides between the reference electrolyte compartment and outside environment serving to minimize diffusion of moisture into or out of the reference electrolyte compartment yet serving to admit sufficient air to allow electrolyte flow from the reference electrolyte compartment through the liquid junction under the influence of gravity and at the same time serving to allow convenient replenishment of reference electrolyte by any liquid delivery means with delivery tip shaped so as to be able to pry open the slit, said slit then closing upon removal of delivery tip by reason of the restorative tendency of the elastomeric septum closure;

whereby the reference electrolyte is kept constant and the standard potential of the reference electrode is thereby stabilized;

whereby the combination glass pH electrode needs no calibration for up to two years.

4. An electrode as in claim 3, where the material of the septum closure comprises a silicone elastomer with a durometer of from about 30 to about 45.

* * * * *